United States Patent [19]

Bates

[11] 3,962,039

[45] June 8, 1976

[54] ANALYTICAL PROCEDURE FOR THYROID HORMONES

[75] Inventor: Harold M. Bates, East Brunswick, N.J.

[73] Assignee: Center for Laboratory Medicine, Metuchen, N.J.

[22] Filed: Aug. 8, 1975

[21] Appl. No.: 603,007

Related U.S. Application Data

[63] Continuation-in-part of Ser. No. 495,869, Aug. 8, 1974, abandoned, which is a continuation-in-part of Ser. No. 463,880, April 24, 1974, abandoned.

[52] U.S. Cl. ..................... 195/103.5 R; 23/230 B; 195/2; 195/5
[51] Int. Cl.² ................... G01N 31/14; G01N 33/16
[58] Field of Search .............. 195/2, 5, 29, 103.5 R, 195/66 B; 23/230 B; 424/2

[56] References Cited

UNITED STATES PATENTS

| | | | |
|---|---|---|---|
| 2,739,099 | 3/1956 | Walaszek | 195/29 |
| 3,730,684 | 5/1973 | Demetriou | 23/230 B |
| 3,770,584 | 11/1973 | Shaltiel et al. | 195/2 |
| 3,806,411 | 4/1974 | Huber et al. | 195/5 |

Primary Examiner—David M. Naff

[57] ABSTRACT

Thyroid hormones in blood serum are determined by admixing a blood serum sample with pepsin, incubating the sample for a period of time to allow pepsin to digest proteins having a thyroid hormone bound thereto and release the thyroid hormone from the proteins, adjusting the resulting mixture to a pH at which pepsin is inactive and assaying the mixture for the released thyroid hormone.

3 Claims, No Drawings

ANALYTICAL PROCEDURE FOR THYROID HORMONES

This application is a continuation-in-part of Ser. No. 495,869, filed Aug. 8, 1974, which in turn is a continuation-in-part of Ser. No. 463,880, filed Apr. 24, 1974, both for the same inventor, both now abandoned.

This invention relates to the concept of destroying a serum or plasma protein molecule, and thus releasing from the protein binding sites a molecule or component or moiety of a material to be subsequently analyzed which is normally tightly bound and is incapable of being detected without extraction by the usual analytical techniques. In addition the improved procedure of this invention destroys substantially all of the binding sites of the protein molecule and eliminates the necessity for the removal of the released component from the reaction mixture prior to analysis.

The serum and plasma proteins, principally albumin, alpha-, beta-, and gamma-globulin, fibrinogen, and the like, have the property of binding to themselves substances in the blood stream such as the thyroid hormones.

According to prior art techniques, a blood serum sample is treated in various ways to remove these components from the serum protein, and ordinarily such removal techniques are only partially complete, requiring the application of a percentage factor to analytical data obtained to approximate a complete analysis.

For example, the thyroid hormones, thyroxine or triiodothyronine are normally present in the serum of human blood bound to a thyrobinding protein, such as an alpha-globulin, known as thyroxing-binding globulin (TBG). To separate the thyroid hormones from their binding protein, it is the usual practice to extract with an alcohol, such as methanol, ethanol or butanol, tetrahydrofurane, or the like. Other techniques include the use of acids, such as aqueous hydrochloric acid of a pH of about 1.5. Once the thyroid hormone is extracted by these procedures, usually to the extent of only about 65–75% complete, the extracted hormone must be carefully separated from the rest of the sample in order to prevent subsequent re-binding to other binding sites on the protein. Techniques relied upon by the prior art include separation by ultra-centrifugation, absorption on an inorganic sorbent material, Sephadex columnar extraction, and the like.

With the improved technique of this invention, complete separation of the above identified components from their binding proteins is accomplished by the use of the proteolytic enzyme, pepsin. This technique not only completely separates the analyzable material from its binding protein, but also substantially destroys the residual binding sites of the protein and thus eliminates, in most instances and for most analytical techniques, the necessity of removing the specific separated substance from the reaction mixture. In addition, any residual enzyme activity, if such were to have any effect on subsequent analytical procedure, can quite easily be destroyed by changing the conditions of the reaction mixture, e.g., by changing the conditions of pH, temperature, etc., to those in which the enzyme is inactive, or by the simple addition to the reaction mixture a specific inhibitor for the proteolytic enzyme.

For use in the competitive protein binding radioassay technique (CPB) or in the radioimmunoassay procedure (RIA) for the thyroid hormones, it is preferred to use the proteolytic enzyme pepsin. There follows an example of such a procedure.

Equal portions of a blood serum sample to be analyzed for thyroid hormones and a pepsin solution containing from about 10,000 to about 80,000 pepsin units per ml is adjusted to a pH of 1.0 with aqueous hydrochloric acid. After incubation at room temperature — 22° to 27° — for 30 minutes, or for 10 minutes at 37° to 45°, all of the thyroid hormones are released from the binding proteins, and all of the binding sites of the thyrobinding proteins are destroyed. This is shown by the following experimental examples.

A human serum pool containing 2.4 micrograms (ug) of thyroxine per 100 ml was enriched with known amounts of L-thyroxine. The serum specimens, so enriched, were treated with equal volumes of a pepsin solution containing from 10,000 to about 80,000 units of pepsin activity per ml adjusted to a pH of 1.0 with aqueous HCl. The samples were then allowed to incubate at room temperature for 30 minutes. To the samples were added barbital buffer at a pH of 8.6 and the buffered solutions were then assayed for thyroxine by the competitive protein binding radioassay technique. The results are reported in TABLE I below:

TABLE I

| Thyroxine Calculated ($\mu$g/100 ml) | Thyroxine Assayed ($\mu$g/100 ml) | Percent Recovery |
|---|---|---|
| 2.4 | 2.5 | 104 |
| 7.4 | 7.3 | 99 |
| 12.4 | 12.6 | 101 |
| 17.4 | 17.2 | 99 |

The results reported above clearly demonstrate that the pepsin digestion destroys all of the thyrobinding protein sites and releases all of the bound thyroxine.

Test tubes, labeled A, B, C and D were used to demonstrate, respectively, the effect of distilled water addition on the binding of $^{125}$I-thyroxine to serum protein, the effect of Hydrochloric acid solution of a pH of 1.0 on the binding of $^{125}$I-thyroxine to serum protein, the effect of an acidic solution of pepsin on the binding of $^{125}$I-thyroxine to serum protein, and the effect of an acidic solution of pepsin on the binding of $^{125}$I-thyroxine to water.

Contents of the tubes are set out in TABLE II below:

TABLE II

| | TUBE A | TUBE B | TUBE C | TUBE D |
|---|---|---|---|---|
| Normal human sera | 0.3 ml | 0.3 ml | 0.3 ml | — |
| $^{125}$I Thyroxine | 0.005 ml | 0.005 ml | 0.005 ml | 0.005 ml |
| Distilled Water | 0.3 ml | — | — | 0.3 ml |
| HCl sol. (ph 1.0) | — | 0.3 ml | — | — |
| Pepsin (3,000 units per 0.3 ml, in HCl sol, pH 1.0) | — | — | 0.3 ml | 0.3 ml |

The four tubes were incubated at room temperature for 30 minutes. At the end of the incubation, 4.0 ml of sodium barbital buffer (0.075 M, pH 8.6) was added and mixed with the contents of each tube. The radioactivity of each tube was measured with a gammacounter. All tubes were found to have the same amount of radioactivity, 64,6000 counts per minute.

Each of the tubes was then transferred to an Amicon ultrafiltration cone with a centrifuge tube attachment.

The tubes were centrifuged for 45 minutes at 2,200 × g at room temperature. The entire ultrafiltrate was collected and the radioactivity counted. The results are set our in TABLE III below:

TABLE III

|  | Radioactivity before Ultrafiltration (cpm) | Radioactivity after Ultrafiltration (cpm) | Thyroxine (1) Bound (5) |
| --- | --- | --- | --- |
| Tube A | 64,600 | 490 | 99.95 |
| Tube B | 64,600 | 29,245 | 54.60 |
| Tube C | 64,600 | 63,555 | 1.62 |
| Tube D | 64,600 | 63,365 | 1.91 |

These results clearly demonstrate that the thyroxine binding sites of the serum proteins are completely destroyed by incubating the serum protein at pH 1.0 for 30 minutes with 3,000 units of pepsin. This is based on the finding that the radioactivity of the water blank and the pepsin-treated serum ultrafiltrates were essentially the same. The results also demonstrate that HCl solution at pH 1.0 without the addition of the pepsin can only partially destroy the thyroxine binding sites.

1. Thyroxine bound to protein was calculated by the equation, a = radioactivity before ultrafiltration,
b = the radioactivity in the ultrafiltrate
% Thyroxine bound = 100 ×(a−b)/a The practive of the novel procedure of the instant invention may also be carried out with the use of a stock solution of the acidic proteolytic enzyme. This solution may be prepared as follows:

Eighty grams of pepsin, USPC, is dissolved in about 1,200 ml of distilled water and adjusted to a pH of 1.0 by adding thereto 6.0 Normal HCl. Glycine Hydrochloride, Glutamic Acid Hydrochloride, Aspartic Acid Hydrochloride, etc., may also be used. The volume of the solution is then adjusted to 1,500 ml with distilled water and a final pH adjustment made, if needed.

An ordinary radioimmunoassay test tube may then be coated with the stock solution, 0.1 ml of a serum to be tested added, the tube mixed, incubated for 30 minutes at toom temperature, neutralized, and then assayed for thyroxine by known techniques.

It is also contemplated that tablets containing the enzyme acid, and the usual inert fillers, such as lactose, etc. may be prepared. One such composition is as follows:

| Pepsin, USP | 1.0 mg |
| --- | --- |
| Glutamic Acid Hydrochlordie | 20.0 mg |
| Lactose | 14.0 mg |

Using standard tabletting techniques, tablets are prepared. One tablet is then dropped into a test tube, a serum sample added, mixed, neutralized and then assayed.

In order to illustrate that the improved technique of this invention gives the same level of accuracy as the prior art techniques when using the standard Competitive Protein Binding Radio Assay procedures for L-Thyroxins, the following experiments were carried out.

A number of hypothyroid, euthyroid and hyperthyoid samples of blood serum were submitted to both the standard prior art technique and to the improved technique of this invention. The Standard technique was as follows:

1. One ml of methanol and 0.5 ml of the serum to be tested were admixed in a radio assay test tube.
2. The sample was then mixed at top speed in a Vortex Mixer for 30 seconds.
3. In a centifuge the tubes were spun for 10 minutes at 1500 times gravity.
4. 0.3 ml of the supernatant was transferred to a radio assay vial containing 4.0 ml of a mixture of the following:
   a. 0.1 ml of $^{125}$I-L-Thyroxine
   b. 0.1 barbital buffer (0.075M–pH 8.6)
   c. 1:350 human serum
5. To each vial there was added one anionic membrane strip
6. The vials were capped and rotated at 33 rpm for exactly 30 minutes at room temperature.
7. The strips were removed, the vials recapped and the radioactivity counted. The count was compared with reference standards.

Using the improved procedure of the instant invention, duplicate samples of the above were treated as follows:

1. To a radio assay test tube there was added 0.1 ml of the sera and 0.1 ml of a pepsin solution in aqueous HCl of pH 1.0 containing approximately 3,000 pepsin units.
2. The test tubes were allowed to stand for 30 minutes at room temperature.
3. Directly to the tube there was then added 4.0 ml of the mixture set out in 4. above.
4. Same as 5 above.
5. Same as 6 above.
6. Same as 7 above.

The results of these comparative tests are set out in TABLE IV below:

TABLE IV

| THYROID STATUS | NO. OF SAMPLES | THYROXINE IN SERUM METHANOL EXTR.* | ($\mu$g/100 ml ± SD) PEPSIN DIGESTION |
| --- | --- | --- | --- |
| HYPOTHYROID SERUM (less than 5 $\mu$g/100 ml) | 18 | 2.4 ± 1.1<br>No significant difference** | 2.0 ± 0.8 |
| EUTHYROID (5–13 $\mu$g/100 ml) | 139 | 8.6 ± 2.0<br>No significant difference** | 8.5 ± 1.7 |
| HYPERTHYROID (greater than 13 $\mu$g/100 ml) | 11 | 17.8 ± 3.9<br>No significant difference** | 16.9 ± 3.0 |

*Corrected for extraction efficiency
**Student's "t" test

These tests clearly demonstrate that when Thyroxine analysis was performed on the same specimens by methanol extraction with a correction for recovery and by pepsin digestion, essentially the same results are obtained.

The present invention is not only useful for measuring the principal thyroid hormone thyroxine (T4), but it is also useful for measuring another important thyroid hormone, triiodothyronine (T3). The concentration of thyroxine in normal human serum is present in amounts ranging from 5.0 to 14.0 micrograms per 100 ml, whereas the concentration of triiodothyronine in normal human serum is present in much smaller quantities, namely 0.09 to 0.20 micrograms/100 ml. This is equal to 90 to 200 nanograms/100 ml. Although triiodothyronine is not bound to serum proteins as tenaciously as thyroxine, it still must be released from the T3-binding sites on serum proteins in order to be assayed. We have found that when human serum is reacted at room temperature with an acidic pepsin solution, the triiodothyronine that is bound to the serum proteins is almost completely released from the protein binding sites. In addition, the binding sites are destroyed, or inactivated irreversibly, so that pepsin-treated serum can be assayed for triiodothyronine by radioimmunoassay. By adjusting the pH of the reaction mixture of pH 1.0 – 2.0 to a basic pH of 8.6, the pepsin is no longer active and does not interfere with the T3 antibody used for the radioimmunoassay of T3.

To demonstrate that this invention can be applied to the radioimmunoassay of triiodothyronine in serum, the following experiment was carried out to measure the recovery of triiodothyronine added to human serum which had been depleted of triiodothyronine by treatment with charcoal.

T3-deficient serum was prepared by treating pooled normal human serum with powdered neutral charcoal (Norit A) at a charcoal concentration of 15% (w/v). The serum-charcoal mixture was shaken for 24 hours at room temperature for 1 hour at 10,000 × g. The resulting serum was further clarified by filtration through a Seitz serum filter (S-3). The clear serum which emerged after filtration contained 35 nanograms of T3/100 ml, which is essentially the limits of detection of T3 by the radioimmunoassay procedure. The pooled serum initially contained 170 nanograms/100 ml.

The charcoal-treated serum was enriched with triiodothyronine at the concentrations listed in the Table below. The assay was carried out in the following manner: One hundred microlites of each serum sample was placed in a 10 × 100 mm glass test tube. One hundred microliters of a solution containing approximately 30,000 units of pepsin in 0.25 N hydrochloric acid was added to each test tube. After mixing the test tubes on a vortex-mixing device, the tubes were allowed to incubate at room temperature for 30 minutes. One milliliter of a solution containing 0.05M barbital buffer, pH 8.6, $^{125}$I-triiodothyronine (35,000 counts per ml), and T3 antiserum (prepared from rabbit and diluted 1/2800 with barbital buffer). The tubes were mixed well on a vortex mixer, and incubated at room temperature for 3 hours. One milliliter of a separating agent (313 Norit A charcoal and 31.3 mg bovine serum albumin in 50 ml phosphate buffer, pH 10.0) was added to each test tube. The tubes were mixed on a vortex mixer and then centrifuged at 3,000 rpm in a clinical centrifuge for 5 minutes at room temperature. The supernatant fluids were decanted into other tubes and the radioactivity was counted. A standard curve was constructed by plotting the radioactivity of each standard (0, 50, 100, 200, 400, and 800 nanograms T3/100 ml) against the quantity of T3. The unkowns were read from the graph.

TABLE V

RECOVERY OF TRIIODOTHYRONINE ADDED TO CHARCOAL-TREATED HUMAN SERUM

| Triiodothyronine Added (nanograms/100 ml) | Triiodothyronine Calculated | (ng/100 ml) Assayed | Percent Recovery |
| --- | --- | --- | --- |
| None | — | 35 | — |
| 90 | 125 | 118 | 94 |
| 180 | 215 | 226 | 105 |
| 270 | 305 | 318 | 104 |
| 360 | 395 | 370 | 94 |
| 450 | 485 | 510 | 105 |

The results of this recovery study clearly show that the use of a pepsin-HCl mixture in the radioimmunoassay of triiodothyronine yields T3 values that are consistent with nearly complete recovery of added T3.

To demonstrate that the treatment of serum with an acidic pepsin solution releases virtually all the triiodothyronine bound to the serum proteins and that adjustment of the pH from about 1.0 to a pH of about 8.6 did not result in the rebinding of the triiodothyronine to the serum proteins, the following experiment was carried out: Four test tubes were labeled A, B, C, and D. The description of each tube and the materials pipetted into each tube is shown below:

MILLILITERS OF MATERIALS ADDED

| TUBE No. | DESCRIPTION | Water | $^{125}$I-T3 | 0.25N HCl | Serum | 3000 units Pepsin |
| --- | --- | --- | --- | --- | --- | --- |
| A | Water Blank | 0.3 | 0.05 | — | — | — |
| B | Serum only | 0.2 | 0.05 | — | 0.10 | — |
| C | Serum + 0.25N HCl | 0.1 | 0.05 | 0.10 | 0.10 | — |
| D | Serum + 0.25N HCl + 3000 units pepsin | — | 0.05 | 0.10 | 0.10 | 0.10 |

The above 4 reaction tubes (A, B, C, and D) were incubated at room temperature for 30 minutes, and, after incubation 4.65 ml of 0.05 M barbital buffer, pH 8.6, was added to each tube. The tubes were mixed well on a vortex mixer. The entire contents of each tube were transferred to an Amicon ultrafiltration cone and centrifuged for 30 minutes at 1,800 × g at room temperature. The ultrafiltrate (2.5 ml) was placed in counting vials and the radioactivity of each ultrafiltrate was measured in a gamma counter. The following results were obtained:

| TUBE NO. | DESCRIPTION | RADIOACTIVITY IN ULTRAFILTRATE (counts/min/2.5 ml) | PERCENT $^{125}$I-T3 RELEASED (relative to water blank = 100%) |
|---|---|---|---|
| A | Water Blank | 32,858 | 100% |
| B | Serum only | 1,086 | 3.3% |
| C | Serum + 0.25N HCl | 8,463 | 25.8% |
| D | Serum + 0.25N HCl + 3000 units pepsin | 31,944 | 97.5% |

These results clearly indicate that treatment of serum with a pepsin-HCl mixture releases isotopically labeled triiodothyronine from serum protein T3-binding sites. The results also show that when the pH of the reaction mixture is adjusted from pH 1.0 to pH 8.6 the isotopically labeled T3 does not rebind to the T3-binding sites on the serum proteins. This is due to the fact that the pepsin-HCl mixture has destroyed the binding sites for T3 on the serum T3-binding molecules.

What is claimed is:

1. A process for the analysis of the thyroid hormone content of a blood serum sample containing a thyroid hormone bound to blood serum proteins, which comprises admixing with a sample of blood serum an effective amount of pepsin at a pH of about 1.0, incubating the sample for a period of time and at a temperature sufficient to allow the pepsin to digest the proteins to which the thyroid hormone is bound and to release the thyroid hormone from said proteins, adjusting the mixture to a pH at which the pepsin is inactive, and assaying the mixture for the released thyroid hormone.

2. A process according to claim 1 wherein said thyroid hormone is thyroxine.

3. A process according to claim 1 wherein said thyroid hormone is triiodothyronine.

* * * * *